(12) United States Patent
Smith

(10) Patent No.: US 8,788,284 B2
(45) Date of Patent: Jul. 22, 2014

(54) METHOD AND SYSTEM USING COMBINED HEALTHCARE-PAYMENT DEVICE AND WEB PORTAL FOR RECEIVING PATIENT MEDICAL INFORMATION

(75) Inventor: Nigel Smith, Silver Spring, MD (US)

(73) Assignee: Visa U.S.A. Inc., San Francisco, CA (US)

( * ) Notice: Subject to any disclaimer, the term of this patent is extended or adjusted under 35 U.S.C. 154(b) by 665 days.

(21) Appl. No.: 11/796,185

(22) Filed: Apr. 27, 2007

(65) Prior Publication Data

US 2007/0282637 A1 Dec. 6, 2007

Related U.S. Application Data

(60) Provisional application No. 60/809,857, filed on May 30, 2006.

(51) Int. Cl.
*G06F 19/00* (2011.01)

(52) U.S. Cl.
USPC ................................................................ 705/3

(58) Field of Classification Search
USPC ........................... 705/2, 3, 4, 40, 67; 707/100
See application file for complete search history.

(56) References Cited

U.S. PATENT DOCUMENTS

| | | | |
|---|---|---|---|
| 4,491,725 A * | 1/1985 | Pritchard | ........................... 705/2 |
| 5,018,067 A | 5/1991 | Mohlenbrock et al. | |
| 5,070,452 A | 12/1991 | Doyle, Jr. et al. | |
| 5,175,416 A | 12/1992 | Mansvelt et al. | |
| 5,235,507 A | 8/1993 | Sackler et al. | |
| 5,301,105 A | 4/1994 | Cummings, Jr. | |
| 5,324,077 A | 6/1994 | Kessler et al. | |
| 5,335,278 A | 8/1994 | Matchett et al. | |
| 5,550,734 A | 8/1996 | Tarter et al. | |
| 5,628,530 A | 5/1997 | Thornton | |
| 5,644,778 A | 7/1997 | Burks et al. | |

(Continued)

FOREIGN PATENT DOCUMENTS

| | | |
|---|---|---|
| AU | 2006203957 | 3/2012 |
| AU | 2006203968 | 3/2012 |

(Continued)

OTHER PUBLICATIONS

Administrative Service of Kansas: ANSI X12N 270/271 Companion Document.*

(Continued)

*Primary Examiner* — John Pauls
(74) *Attorney, Agent, or Firm* — Loeb & Loeb LLP

(57) ABSTRACT

Embodiments of systems and methods in accordance with the present invention relate to a centralized portal for making healthcare information of a patient accessible to a plurality of entities, including but not limited to the patient himself/herself, healthcare providers authorized by the patient, and healthcare payers (insurance carriers) authorized by the patient. In one embodiment, the portal comprises a website associated with a portable consumer device (such as a HSA magnetic stripe credit/debit card) of the patient, and hosted on a server accessible over the world wide web or another computer network. The patient sets a privacy level associated with his or her medical record on the host site, the privacy level granting certain entities (for example healthcare providers or insurance carriers) access to particular medical records of the patient. Upon presenting the portable consumer device to an authorized healthcare provider, medical information previously transmitted through a payment processing network may be received at the authorized healthcare provider.

25 Claims, 7 Drawing Sheets

(56) References Cited

U.S. PATENT DOCUMENTS

| | | |
|---|---|---|
| 5,710,578 A | 1/1998 | Beauregard et al. |
| 5,832,447 A | 11/1998 | Rieker et al. |
| 5,915,241 A | 6/1999 | Giannini |
| 5,965,860 A | 10/1999 | Oneda |
| 5,995,939 A | 11/1999 | Berman et al. |
| 6,012,035 A | 1/2000 | Freeman, Jr. et al. |
| 6,044,352 A | 3/2000 | Deavers |
| 6,082,776 A | 7/2000 | Feinberg |
| 6,112,183 A | 8/2000 | Swanson et al. |
| 6,151,588 A | 11/2000 | Tozzoli et al. |
| 6,208,973 B1 * | 3/2001 | Boyer et al. ............... 705/2 |
| 6,332,133 B1 | 12/2001 | Takayama |
| 6,343,271 B1 | 1/2002 | Peterson et al. |
| 6,401,079 B1 | 6/2002 | Kahn et al. |
| 6,529,884 B1 | 3/2003 | Jakobsson |
| 6,629,081 B1 | 9/2003 | Cornelius et al. |
| 6,850,901 B1 | 2/2005 | Hunter et al. |
| 6,877,655 B1 | 4/2005 | Robertson et al. |
| 6,915,265 B1 | 7/2005 | Johnson |
| 6,988,075 B1 | 1/2006 | Hacker |
| 7,072,842 B2 | 7/2006 | Provost et al. |
| 7,174,302 B2 | 2/2007 | Patricelli et al. |
| 7,295,988 B1 | 11/2007 | Reeves |
| 7,428,494 B2 | 9/2008 | Hasan et al. |
| 7,650,308 B2 | 1/2010 | Nguyen et al. |
| 7,752,096 B2 | 7/2010 | Santalo et al. |
| 7,769,599 B2 | 8/2010 | Yanak et al. |
| 7,774,273 B2 | 8/2010 | Neal et al. |
| 7,792,688 B2 | 9/2010 | Yanak et al. |
| 7,866,548 B2 | 1/2011 | Reed et al. |
| 7,925,518 B2 | 4/2011 | Lee et al. |
| 7,996,260 B1 | 8/2011 | Cunningham et al. |
| 2001/0037295 A1 | 11/2001 | Olsen |
| 2001/0053986 A1 | 12/2001 | Dick |
| 2002/0002534 A1 | 1/2002 | Davis et al. |
| 2002/0002536 A1 | 1/2002 | Braco |
| 2002/0019808 A1 | 2/2002 | Sharma |
| 2002/0032583 A1 | 3/2002 | Joao |
| 2002/0128863 A1 | 9/2002 | Richmond |
| 2002/0138309 A1 | 9/2002 | Thomas, Jr. |
| 2002/0147678 A1 | 10/2002 | Drunsic |
| 2002/0152180 A1 | 10/2002 | Turgeon |
| 2002/0198831 A1 * | 12/2002 | Patricelli et al. ............... 705/40 |
| 2003/0009355 A1 | 1/2003 | Gupta |
| 2003/0037054 A1 * | 2/2003 | Dutta et al. ............... 707/100 |
| 2003/0040939 A1 | 2/2003 | Tritch et al. |
| 2003/0055686 A1 | 3/2003 | Satoh et al. |
| 2003/0193185 A1 | 10/2003 | Valley et al. |
| 2003/0200118 A1 | 10/2003 | Lee et al. |
| 2003/0212642 A1 | 11/2003 | Weller et al. |
| 2003/0225693 A1 | 12/2003 | Ballard et al. |
| 2004/0006489 A1 | 1/2004 | Bynon |
| 2004/0006490 A1 | 1/2004 | Gingrich et al. |
| 2004/0039693 A1 | 2/2004 | Nauman et al. |
| 2004/0054935 A1 | 3/2004 | Holvey et al. |
| 2004/0103000 A1 * | 5/2004 | Owurowa et al. ............... 705/2 |
| 2004/0111345 A1 | 6/2004 | Chuang et al. |
| 2004/0128201 A1 | 7/2004 | Ofir et al. |
| 2004/0138999 A1 | 7/2004 | Friedman et al. |
| 2004/0148203 A1 | 7/2004 | Whitaker et al. |
| 2004/0172312 A1 | 9/2004 | Selwanes et al. |
| 2004/0186746 A1 * | 9/2004 | Angst et al. ............... 705/3 |
| 2004/0210520 A1 | 10/2004 | Fitzgerald et al. |
| 2004/0225567 A1 | 11/2004 | Mitchell et al. |
| 2004/0254816 A1 | 12/2004 | Myers |
| 2005/0010448 A1 | 1/2005 | Mattera |
| 2005/0015280 A1 | 1/2005 | Gabel et al. |
| 2005/0033609 A1 * | 2/2005 | Yang ............... 705/2 |
| 2005/0038675 A1 | 2/2005 | Siekman et al. |
| 2005/0065819 A1 | 3/2005 | Schultz |
| 2005/0065824 A1 | 3/2005 | Kohan |
| 2005/0071194 A1 | 3/2005 | Bormann et al. |
| 2005/0119918 A1 | 6/2005 | Berliner |
| 2005/0182721 A1 | 8/2005 | Weintraub |
| 2005/0187790 A1 | 8/2005 | Lapsker |
| 2005/0187794 A1 | 8/2005 | Kimak |
| 2005/0209893 A1 | 9/2005 | Nahra et al. |
| 2005/0211764 A1 | 9/2005 | Barcelou |
| 2005/0246292 A1 | 11/2005 | Sarcanin |
| 2005/0273387 A1 | 12/2005 | Previdi |
| 2005/0288964 A1 | 12/2005 | Lutzen et al. |
| 2006/0010007 A1 | 1/2006 | Denman et al. |
| 2006/0106645 A1 | 5/2006 | Bergelson et al. |
| 2006/0106646 A1 | 5/2006 | Squilla et al. |
| 2006/0111943 A1 | 5/2006 | Wu |
| 2006/0129427 A1 | 6/2006 | Wennberg |
| 2006/0129435 A1 | 6/2006 | Smitherman et al. |
| 2006/0136270 A1 * | 6/2006 | Morgan et al. ............... 705/3 |
| 2006/0149529 A1 | 7/2006 | Nguyen et al. |
| 2006/0149603 A1 | 7/2006 | Patterson et al. |
| 2006/0149670 A1 | 7/2006 | Nguyen et al. |
| 2006/0161456 A1 * | 7/2006 | Baker et al. ............... 705/2 |
| 2006/0173712 A1 * | 8/2006 | Joubert ............... 705/2 |
| 2006/0184455 A1 * | 8/2006 | Meyer et al. ............... 705/67 |
| 2006/0206361 A1 | 9/2006 | Logan, Jr. |
| 2006/0224417 A1 | 10/2006 | Werner |
| 2006/0229911 A1 | 10/2006 | Gropper et al. |
| 2006/0235761 A1 | 10/2006 | Johnson |
| 2007/0005403 A1 | 1/2007 | Kennedy et al. |
| 2007/0027715 A1 | 2/2007 | Gropper et al. |
| 2007/0061169 A1 | 3/2007 | Lorsch |
| 2007/0106607 A1 | 5/2007 | Seib et al. |
| 2007/0125844 A1 | 6/2007 | Libin et al. |
| 2007/0143215 A1 | 6/2007 | Willems |
| 2007/0282637 A1 | 12/2007 | Smith |
| 2008/0010096 A1 | 1/2008 | Patterson et al. |
| 2008/0071646 A1 | 3/2008 | Hodson et al. |
| 2008/0140447 A1 | 6/2008 | Pourfallah et al. |
| 2008/0147518 A1 | 6/2008 | Haider et al. |
| 2008/0177574 A1 | 7/2008 | Gonzalez et al. |
| 2008/0319904 A1 | 12/2008 | Carlson et al. |
| 2010/0100484 A1 | 4/2010 | Nguyen et al. |
| 2010/0332251 A1 | 12/2010 | Yanak et al. |
| 2011/0178816 A1 | 7/2011 | Lee et al. |

FOREIGN PATENT DOCUMENTS

| | | |
|---|---|---|
| EP | 1834275 | 9/2007 |
| EP | 1834314 | 9/2007 |
| EP | 1856663 | 11/2007 |
| EP | 2030163 | 3/2009 |
| EP | 2035990 | 3/2009 |
| HK | 1107164 | 3/2008 |
| HK | 1107172 | 3/2008 |
| HK | 1108752 | 5/2008 |
| JP | 2005124991 | 5/2005 |
| JP | 2008545210 | 12/2008 |
| JP | 2009541864 | 11/2009 |
| KR | 1020040028017 | 4/2004 |
| KR | 1020050099707 | 10/2005 |
| KR | 1020050094938 | 7/2006 |
| KR | 1020070041183 | 4/2007 |
| WO | WO99/22330 | 5/1999 |
| WO | WO01/06468 | 1/2001 |
| WO | WO03/073353 | 9/2003 |
| WO | WO2006/074285 | 7/2006 |

OTHER PUBLICATIONS

Supplemental European Search Report for European Patent Application EP 07798894.*

Companion Guide 835 Health Care Claim Payment/Advice, Convansys, Jun. 24, 2004 XP002564865 http://www.njelkids.com/UL/pdf/NJ_835v1_20040820-2.pdf.

Hammond, W Edward and Cimino, James "Standards in Medical Informatics: Computer Applications in Health Care and Biomedicine," 2000 Springer, NY XP002564866, pp. 226-276.

Classen, David et al.; "The Patient safety Insitute demonstration Project: A Model for Implementing a Local Health information Infrastructure"; 2004, Journal of Healthcare Information Management, vol. 19, No. 4, pp. 75-86.

"Patient Safety Institute: Economic Value of a Community Clinical Information Sharing Network, Part 1: Value to Payers (Private, Medi-

(56) References Cited

OTHER PUBLICATIONS care, Medicaid and self-Insured Employers) and the Uninsured"; White Paper prepared by Emerging Practives First consulting Group, 2004. pp. 1-18.

"Visa Introduces Next Generation B2B Payment Service" downloaded on www.corporate.visa.com/md/nr/press136.jsp, Feb. 2, 2007, pp. 1-3.

"Visa USA Small Business & Merchants, Visa ePay—How it Works" downloaded on www.usa.visa.com/business/accepting_visa/payment_technologies/epay_how_it_works.html, Feb. 2, 2007, p. 1.

"Visa USA Small Business & Merchants, Visa epay—Participating Financial Institutes" downloaded on www.usa.visa.com/business/accepting_visa/payment_technologies/epay_fi.html , at Feb. 2, 2007, p. 1.

"Visa ePay" downloaded on www.usa.visa.com/business/accepting_visa/payment_technologies/epay.html, Feb. 2, 2007, p. 1.

"Welcome to American Express Healthpay Plus Works, What is Pay Plus" downloaded on www.152.americanexpress.com/entcampweb/payment_technologies/epay_how_it_works.jsp, Feb. 2, 2007, pp. 1-2.

"Visa USA Small Business & marchants, Visa ePay—Credit counseling Automation" downloaded on www.usa.visa.com/business/accepting_visa/payment_technologies/epay_credit_counseling.html, Feb. 2, 2007, pp. 1-3.

"Visa Introduces Next Generation B2Bpayment Service" downloaded on www.sellitontheweb.com/ezine/news0569.shtml, Feb. 2, 2007, pp. 1-4.

"Welcome to American Express Healthpay Plus(SM)", What is HealthPay Plus downloaded on www.152.americanexpress.com/entcampweb/whatishealthpayplus.jsp at Feb. 2, 2007, pp. 1-5.

Supplementary European Search Report for EP 06717481, Jan. 8, 2010.

International Search Report for PCT/US2006/00288.

Supplementary European Search Report for EP 06717470, Mar. 10, 2010.

International Search Report for PCT/US2006/00274.

Supplementary European Search Report for EP 06717482, May 25, 2011.

Supplementary European Search Report for European Patent Application EP 07798894.

Recal Introduces WebSentry Reducing the Risk of Fraud for Internet Transactions; WebSentry Offers System Integrators Cost Effective SET Compliance for E-Commerce—Canada Corporation News May 26, 1999.

AssureBuy Newsletter—vol. 1, Issue 1, "Topic: Level III Transactional Detail". Accessed on internet archive at http://web.archive.org/web/20030713220249/http://assurebuy.com/newsletter01_01.html on Apr. 30, 2013. Content available according to WayBayck Machine on Jul. 13, 2003.

Babcock, Charles; "New Claim Game"; Information Week; Feb. 9. 2004.

Young, Mark; "Scripps health automates its claims forms processing"; Today—The Journal Of Work Process Improvement; Feb. 1999.

International Preliminary Report on Patentability completed on Oct. 11, 2011 corresponding to PCT/US07/84179.

International Search Report mailed on May 5, 2008 corresponding to PCT/US07/84179.

International Preliminary Report on Patentability issued on Sep. 25, 2007 corresponding to PCT/US06/000288.

U.S. Appl. No. 60/641,483; entitled "Method and System for Determining Healthcare Eligibility", filed Jan. 4, 2005.

U.S. Appl. No. 60/641,597; entitled "Auto Adjudication for over-the-counter transactions", filed Jan. 4, 2005.

U.S. Appl. No. 60/641,464; entitled "Method for encoding messages between two devices for transmission over standard online payment networks", filed Jan. 4, 2005.

U.S. Appl. No. 60/834,584; entitled "Electronic payment delivery service", filed Jul. 31, 2006.

U.S. Appl. No. 60/812,266; entitled "System and method using extended authorization hold period", filed Jun. 8, 2006.

* cited by examiner

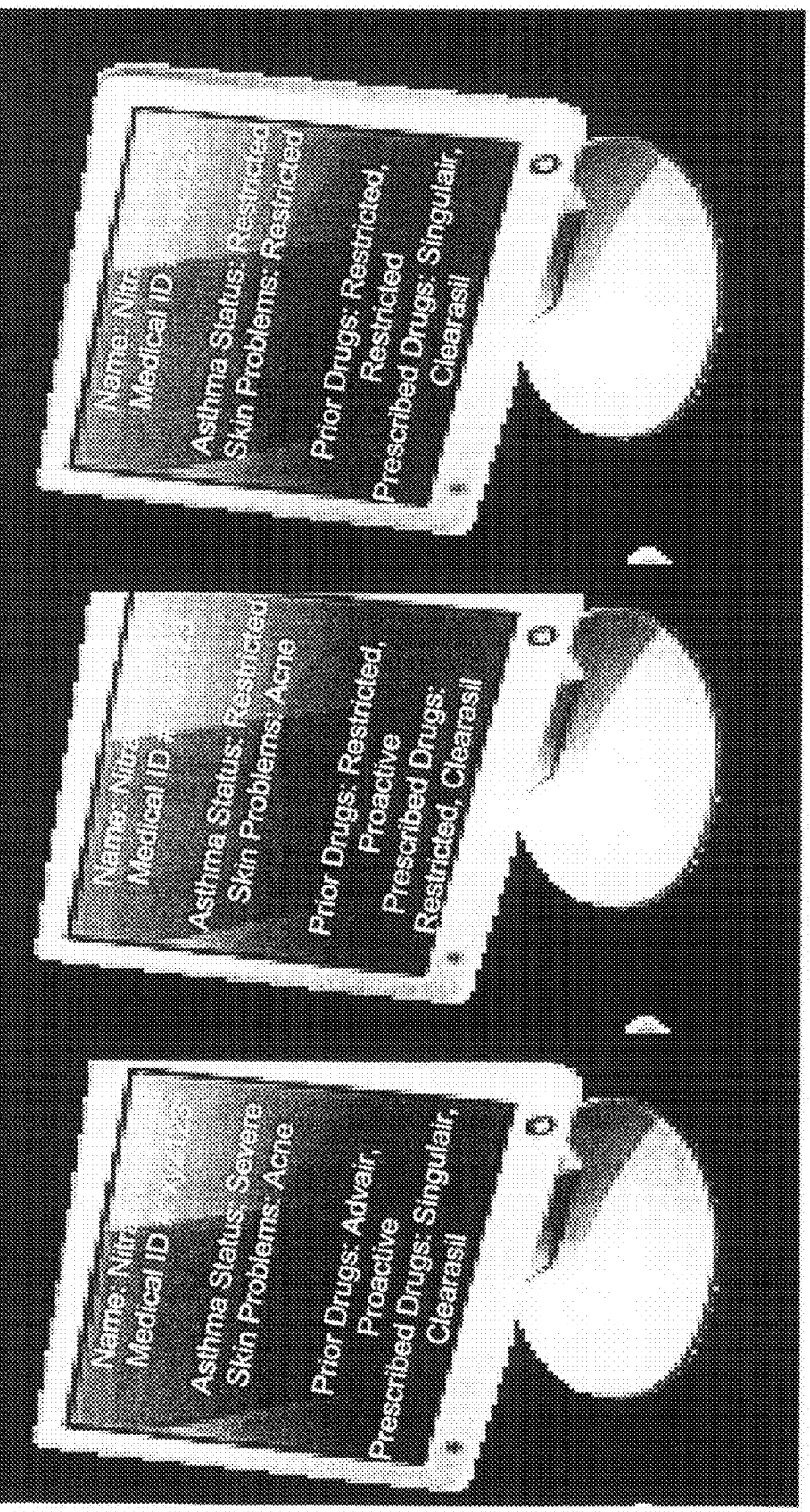

METHOD AND SYSTEM USING COMBINED HEALTHCARE-PAYMENT DEVICE AND WEB PORTAL FOR RECEIVING PATIENT MEDICAL INFORMATION

CROSS-REFERENCES TO RELATED APPLICATIONS

The instant nonprovisional patent application claims priority to U.S. Provisional Patent Application No. 60/809,857, filed May 30, 2006 and incorporated by reference herein in its entirety for all purposes.

BACKGROUND

A recent trend in healthcare insurance is the emergence of high deductible healthcare plans. Specifically, as employers try to control year-over-year increases in providing their employees with a health insurance benefit, many small and medium-size companies are turning to health plans with higher deductible amounts. Deductibles of $1,000 for individual coverage and $2,000 for family coverage are typical of high deductible plans.

To fill the deductible gap, some employers will fund a portion of the deductible amount through a Health Reimbursement Arrangement (HRA) or Health Savings Account (HSA). With HSAs, employees can also contribute funds up to the amount of their deductible (if the plan meets IRS requirements for a high deductible plan). Another source for the payment of high healthcare coverage deductibles, are Flexible Spending Accounts (FSA) which allow the allocation of pre-tax dollars toward healthcare expenses.

In view of growing responsibility of the individual patient in monitoring and paying for health care expenses, methods and systems promoting ease of electronic access to the healthcare records are desirable, as are systems conferring the ability of the individual to easily and rapidly control the parties having access to those healthcare records.

Another recent development in the healthcare field is the implementation of the Health Insurance Portability and Accountability Act (HIPAA). Enacted by Congress in 1996, Title I of HIPAA sets forth a number of requirements addressing the security and privacy of healthcare data communicated between different covered entities, for example a healthcare provider and a healthcare insurance company.

In addition, Title II of HIPAA dictates the adoption of standardized electronic data interchange (EDI) message formats to exchange information, and the utilization of electronic forms of payment. For example, a HIPAA message type 270 ("HIPAA 270") describes a format for an electronic benefit inquiry message sent from a healthcare provider to an healthcare insurance carrier. In turn, a HIPAA message type 271 ("HIPAA 271") describes a format for a response to the benefit inquiry message, that is returned to the healthcare provider by the health insurance carrier. Examples of other HIPAA sections describing particular electronic message formats include a HIPAA message type 837 ("HIPAA 837") which is a healthcare claim message to insurer, and a HIPAA message type 835 ("HIPAA 835") which is an electronic remittance from insurer to healthcare provider. HIPAA adopts some portions of the above message formats from standards set by the American National Standards Institute (ANSI) Accredited Standards Committee (ASC). Accordingly, the HIPAA message types may refer to various portions of the ANSI standards. For example, HIPAA 271 may refer to some portion of ANSI X12N 271, HIPAA 835 may refer to some portion of ANSI X12N 835, and HIPAA 837 may refer to some portion of ANSI X12N 837.

In view of the above, banks, healthcare companies, and third party processing providers have an incentive to bring to the healthcare marketplace the degrees of reliability, interoperability, security, and automation that exists in banking and the traditional payments arena.

SUMMARY

Embodiments of systems and methods in accordance with the present invention relate to a centralized portal making healthcare information of a patient accessible to a various entities, including but not limited to the patient himself/herself, healthcare providers authorized by the patient, and healthcare payers (insurance carriers) authorized by the patient. In one embodiment, the portal includes a website associated with a portable consumer device (such as a HSA magnetic stripe debit/credit card) of the patient, and hosted on a server accessible over the world wide web or another computer network. The patient sets a privacy level associated with his or her medical record on the host site, the privacy level granting certain entities (for example healthcare providers or insurance carriers) access to the medical record of the patient. Upon presenting the portable consumer device to an authorized healthcare provider, medical information previously transmitted through an electronic payment processing network may be received at the authorized healthcare provider.

An embodiment of a method in accordance with the present invention comprises setting a privacy level associated with a patient's medical record on a host site, wherein the host site is associated with a portable consumer device, and wherein the privacy level provides certain entities, including healthcare providers with the ability to access the patient's medical record. The portable consumer device is presented to a healthcare provider who has access to the medical record, medical information is received at the provider, wherein the medical information is transmitted through a payment processing network.

An embodiment of an apparatus in accordance with the present invention, comprises, a host computer including a processor in electronic communication with a computer readable storage medium. The computer readable storage medium having code stored thereon to direct the processor to, set a privacy level associated with a patient's medical record on a host site, wherein the host site is associated with a portable consumer device, and wherein the privacy level provides certain healthcare providers with the ability to access the patient's medical record, and to send information pertaining to the patient's medical record to a healthcare provider who has access to the medical record, after the patient presents An embodiment of a computer readable medium in accordance with the present invention, comprises, code for setting a privacy level associated with a patient's medical record on a host site, wherein the host site is associated with a portable consumer device, and wherein the privacy level provides certain healthcare providers with the ability to access the patient's medical record; and code for sending information pertaining to the patient's medical record to a healthcare provider who has access to the medical record, after the patient presents the portable consumer device to a healthcare provider.

An embodiment of a method for management of healthcare information in accordance with the present invention, comprises the steps of establishing a plurality of access authorization levels based on the type of healthcare information needed for a patient by a healthcare provider, authorizing access to the healthcare information with a portable device, wherein the patient provides the healthcare provider with access to the healthcare information using the portable device and wherein the level of access is based on the established access authorization levels, and providing payment for the service using the portable device.

These and other embodiments of the invention are described in further detail below.

BRIEF DESCRIPTION OF THE DRAWINGS

FIG. 1B is a simplified schematic diagram shown exemplary screen shots for different privacy settings.

DETAILED DESCRIPTION

Embodiments of systems and methods in accordance with the present invention relate to a centralized portal for making healthcare information of a patient accessible to a plurality of entities, including but not limited to the patient himself/herself, healthcare providers authorized by the patient, healthcare payers (insurance carriers) authorized by the patient, and other entities authorized by the patient. In one embodiment, the portal comprises a website (an example of a host site) associated with a portable consumer device (such as a HSA magnetic stripe debit/credit card) of the patient, and hosted on a server accessible over the world wide web or another computer network. The patient sets a privacy level associated with his or her medical record on the host site, the privacy level granting certain entities (for example healthcare providers or insurance carriers) access to the medical record of the patient. Upon presenting the portable consumer device to an authorized healthcare provider, medical information previously transmitted through a payment processing network may be received at the authorized healthcare provider.

Figure 1:
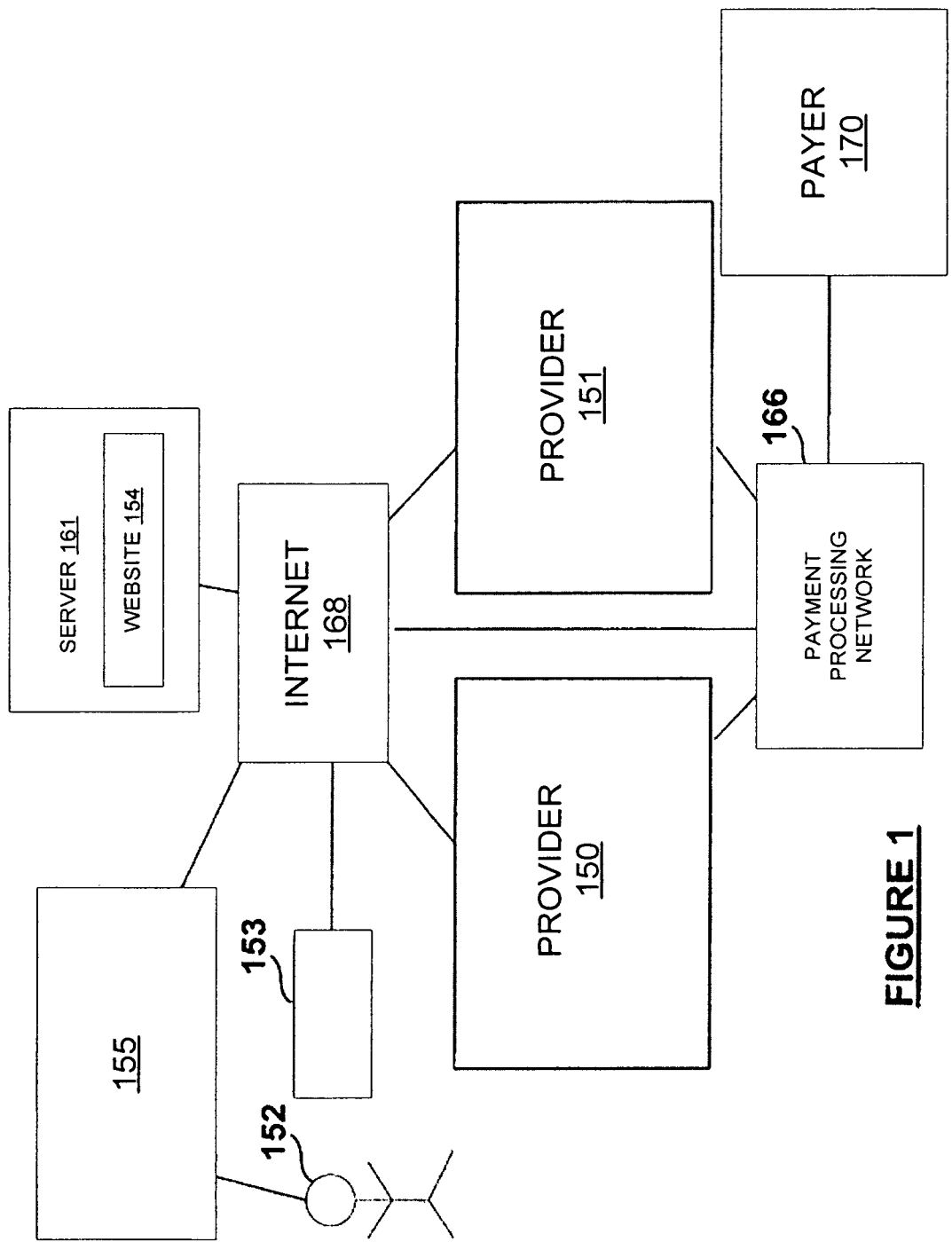
FIG. 1 shows a simplified schematic diagram illustrating interactions between various entities in accordance with the teachings of the present invention.
Figure 1A:
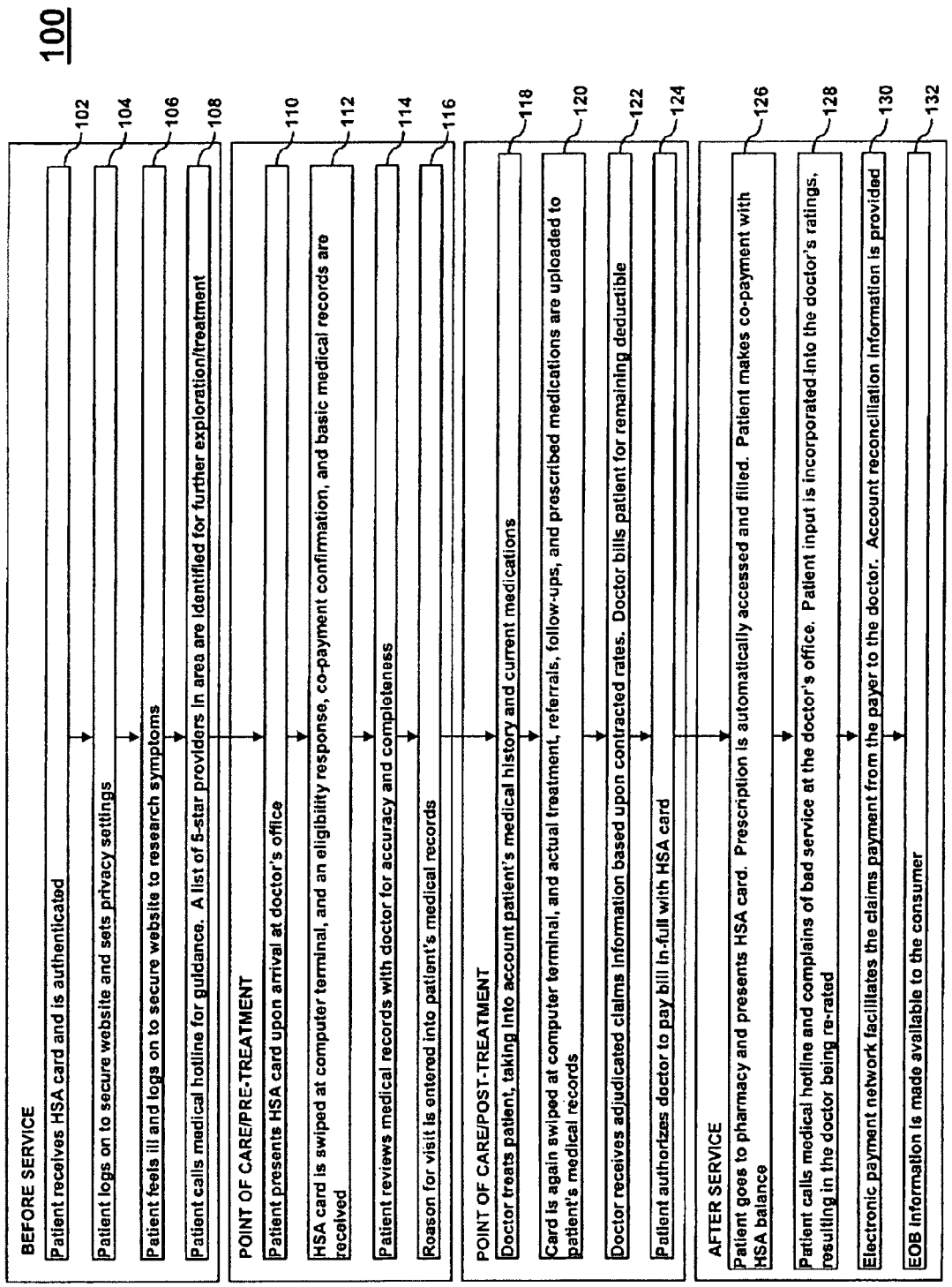
FIG. 1A shows a simplified flow diagram of various steps illustrated in FIG. 1.

FIG. 1 shows a simplified schematic diagram illustrating the interaction between different entities in accordance with an embodiment of the present invention. FIG. 1A shows a simplified diagram illustrating flows of information between the entities shown in FIG. 1. Embodiments of the invention may take place in the order shown in FIG. 1A, or may take place in any other suitable order.

Steps 102-108 of flow 100 take place before healthcare services have been rendered to a patient by a healthcare provider. In step 102, before seeking service from a healthcare provider 150 and 151, a patient 152 receives a portable consumer device 153 and authenticates it.

In accordance with one particular embodiment, the portable consumer device 153 is a magnetic stripe credit, debit, prepaid, or stored value card. In accordance with alternative embodiments, however, the portable consumer device 153 may take other forms. For example, the portable consumer devices can be hand-held and compact so that they can fit into a consumer's wallet and/or pocket (e.g., pocket-sized). The portable consumer devices may include smart cards (with a microprocessor), a keychain device, etc. Other examples of portable consumer devices include cellular phones, personal digital assistants (PDAs), pagers, payment cards, security cards, access cards, smart media, transponders, and the like. The portable consumer devices 153 can also be debit devices (e.g., a debit card), credit devices (e.g., a credit card), or stored value devices (e.g., a stored value card). In some embodiments, the portable consumer devices 153 may be re-writeable so that values associated with the portable consumer devices 153 are stored on them. In other embodiments, the values associated with the portable consumer devices may be stored at a server operated by or at an issuer. An "issuer" is typically a financial institution, such as a bank, that issues the portable consumer device to the patient. In some embodiments, the portable consumer devices may function as payment devices that can be used to access both payment accounts (e.g., credit card accounts) and healthcare spending accounts (e.g., flexible spending accounts or health savings accounts).

In step 104, patient 152 uses a personal computer or client computer 155 and logs on to a secure website 154 hosted at a server 161 and sets privacy settings for his or her account. The existence of the account on the secure website 154 grants one or more healthcare providers, such as providers 150 and 151, with the ability to access the patient's medical records. The patient can control the privacy settings that are established, such that various levels of information may be accessed by other entities.

For example, FIG. 1B is a simplified schematic diagram shown exemplary screen shots for different privacy settings. One privacy setting may confer an outside entity unrestricted access to information on the website (e.g. primary care physician or hospital emergency room). A different privacy setting may confer an outside entity only with a listing of prior medications and treatments related to the specialist being see, but may exclude access to non-directly relevant medical information (e.g., dermatologist). Still another privacy setting may confer an outside entity only with a listing of prescribed medications and treatments, but may exclude access to all other medical information (e.g., pharmacist view).

The server 161 may be embodied by one or more computational apparatuses, which can service the requests of one or more client computers. Typically, the server 161 is a powerful computer or cluster of computers that behave as a single computer. For example, the server 161 can be a mainframe computer, a minicomputer, or a minicomputer cluster. In another example, the server 161 may include one or more database servers and one or more Web servers. The server 161 may service the requests of one or more client computers.

After the patient 152 uses a client computer or personal computer 155 and sets his or her privacy settings on the website 154, the server 161 may send notification messages to the providers 150 and/or 151 indicating that they are able to access the patient's medical information.

At some point in time, in step 106 patient 152 feels ill and logs onto the secure website 154 in order to research his or her symptoms. Uncertain of the exact diagnosis, in step 108 patient 152 calls a medical hotline at the healthcare information provider 155 for guidance. In response, a list of consumer rated (such as five-star) healthcare providers in user's geographic area is generated and shared with the patient to allow the patient to further explore and/or attend for treatment of symptoms. If the patient has not already set privacy settings, the patient may thereafter set privacy settings thereby allowing specific providers with the ability to access their medical information. Prompts such as pop up windows, drop down menus, etc. may be used to prompt the patient to provide desired privacy settings.

Steps 110-116 of process flow 100 take place at the point of care, prior to treatment. In step 110, the patient 152 goes to a particular provider, such as provider 150, which may be a doctor, to seek treatment. Other examples of providers include hospitals, dentists, eyecare specialists, etc. The provider 150 is a healthcare provider to whom the patient 152 has previously granted access to his or her medical records on the secure website 154.

In step 112, the patient 152 presents his portable consumer device 153 to the provider 150 upon arrival at the doctor's office. If the portable consumer device 153 is a payment card, such as a magnetic stripe credit card or combined payment-healthcare spending account card, then the portable consumer device 153 is swiped at a computer terminal (not shown) at the office of the provider 150, and information therefrom is communicated across an payment processing network 166 to a payer 170. Within a short time (e.g., less than 30 seconds), in step 114 an eligibility response, co-payment confirmation, and basic medical record may be communicated to the provider 150 over the payment processing network 166, which may be a closed system inaccessible to the general public. An exemplary payment processing network may be VisaNet operated by Visa®. Payment processing networks have capabilities for communications via private telecommunication network facilities, as well as the ability to process transactions in Internet Protocol (IP) formats to facilitate the exchange of transactions between and amongst private networks and open networks, such as the Internet.

Figure 2:
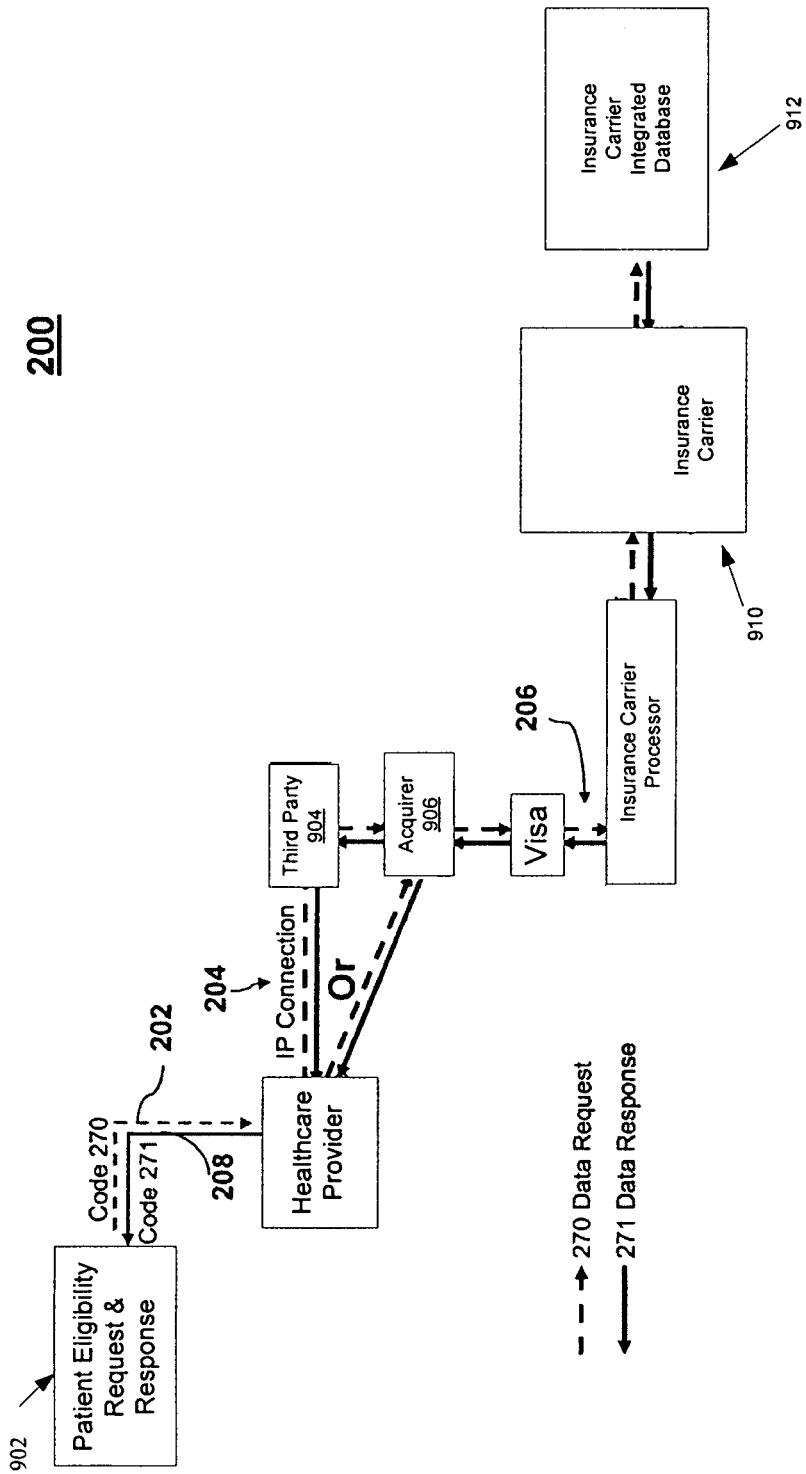
FIG. 2 shows a simplified schematic diagram of an example of a processing flow for eligibility requests in accordance with the teachings of the present invention.

Specifically, FIG. 2 shows a simplified schematic diagram of an example of a processing flow 200 for eligibility requests in accordance with an embodiment of the present invention. In step 202, a point of service (POS) terminal 902 associated with provider 150 submits a HIPAA 270 eligibility request message to an insurance carrier 910. In step 204, the HIPAA 270 eligibility request message is received by a third party interface 904, or directly by an acquirer 908 (e.g., through a virtual POS connection). The acquirer 908 may be a financial institution such as a bank that is associated with the healthcare provider 150. In step 206, the HIPAA 270 eligibility request message is routed from the third party interface 904 or the acquirer 906 to the appropriate insurance carrier 910 (Payer) through the previously described payment processing network (not shown), which may (or may not) involve additional third party processors 908. The insurance carrier 910 may access a database 912, which may contain information about the patient's eligibility. As shown by the solid arrows going from the insurance carrier database 912 back to the POS terminal 902, insurance carrier 910 validates patient eligibility, and routes a HIPAA 271 eligibility status message 208 back to healthcare provider's POS terminal 902.

Returning to the process flow of FIG. 1, once eligibility has been determined, in step 116 the patient 152 then reviews the medical record with the provider 150 (or the doctor's staff), for accuracy and completeness. The reason for the visit is entered into patient's medical records on the secure website 154. A client computer terminal (not shown) at the office of the provider 150 may be used for this purpose.

Steps 118-124 of process flow 100 take place at the point of care, post-treatment. In step 118, the provider 150 treats the patient 152, taking into account the patient's medical history and current medications. In step 120, the portable consumer device 153 is again swiped at the computer terminal in the office of the provider 150, and information such as actual treatment, referrals, follow-ups, and prescribed medications are uploaded to the patient's medical records stored using the secure website 154. Such transactions may be transmitted either via private network communications, or over an open network in IP format by a payment processing network, like VisaNet™.

Again within a short time (i.e. 30 seconds), in step 122 and in response to the second swipe of the portable consumer device 153, the doctor (provider 150) receives from the payer 170 over the payment processing network 166, adjudicated claims information based upon contracted rates. The doctor then bills the patient 152 for any remaining deductible. If desired, in step 124, the patient 152 authorizes the provider 150 to pay the bill in-full with the portable consumer device 153 (e.g. with a HSA payment card).

Steps 126-132 take place after the doctor's service has been performed. In step 126 patient 152 may go to a second healthcare provider, such as provider 151 (for example a pharmacy or laboratory) and may present the portable consumer device 153 to the provider 151. For example, when the provider 151 is a pharmacy, the prescription is automatically accessed and filled, with the pharmacist having access to the information portal of website 154 in order to double check the appropriateness of the medication for the treatment that has been performed. The patient 152 then makes a co-payment at the provider 151.

Once at home, in step 128 the patient 152 may again call the medical hotline of the healthcare information provider 155, this time to provide feedback upon the care that has been provided, such as to provide comments on the service. For example, the patient 152 may provide information about bad service at the office of the provider 150. The comments of the patient 150 then incorporated into the rating of the provider 150 on the secure website 154, resulting in the provider 150 being re-rated, which in this specific example would be to change the rating from 5-star to a 4.5-star provider. By facilitating ongoing rating of the performance of the provider, readily accessible at the centralized healthcare portal, embodiments of methods and systems in accordance with the present invention help ensure a high quality of service.

In step 130, a payment processing organization, such as Visa®, that administers the payment processing network 166 may then facilitate the payment of claims from payer 170 to the provider 150. The payment processing network 166 may be operatively connected to various acquirers and issuers. Account reconciliation information may be provided through the secure website 154. Of course, the scope of the present invention is not limited to payments over a network administered by Visa®, and other payment methods such as automated clearing house transactions or payment processing networks could alternatively be used.

Figure 3:
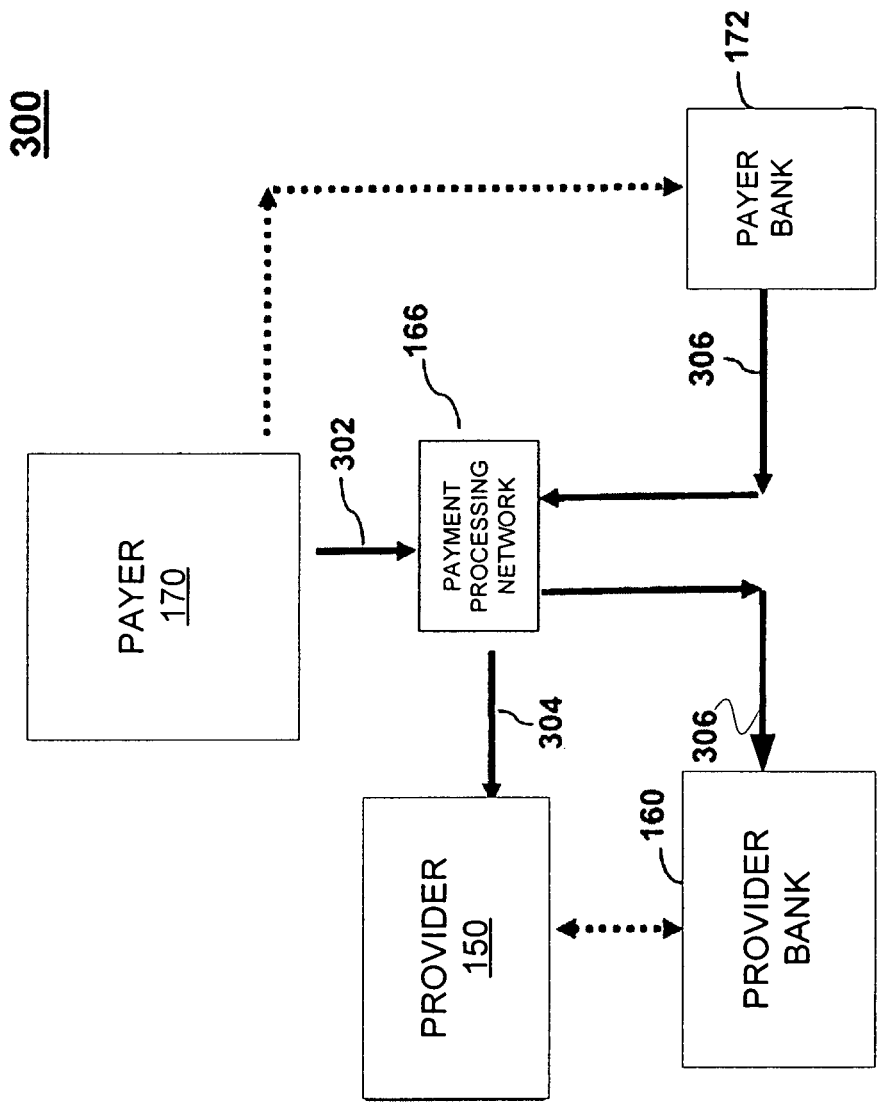
FIG. 3 shows a simplified schematic diagram of an example of a processing flow for payment of claims in accordance with the teachings of the present invention.

Specifically, FIG. 3 shows a simplified schematic diagram of an example of a processing flow 300 for payment of claims utilizing the payment processing network 166. In step 302, the payer 170 (e.g., an insurance company) remits a HIPAA-compliant §835 claim payment message to the payment processing network 166 for healthcare services rendered. In step 304, the payment processing network 166 creates a file containing payer payments to the provider 150, and makes health care claim advice data available to the provider 150. In step 306, the payment processing network 166 transfers funds from the bank account of the payer 170 at a payer bank 172 to the bank account of the provider 150 at a provider bank 160 via the payment processing network 166. The payment processing network 166 also routes appropriate files to the provider bank 160 to pay for services rendered by the provider 150. The provider 150 may thereafter access funds that are deposited in the account of the provider 150 at the provider bank 160. Although in this specific embodiment, two different banks are shown, alternative embodiment are contemplated, where the provider bank and the payer bank are the same bank and, hence, funds are transferred between two accounts within the same banking organization.

Figure 4:
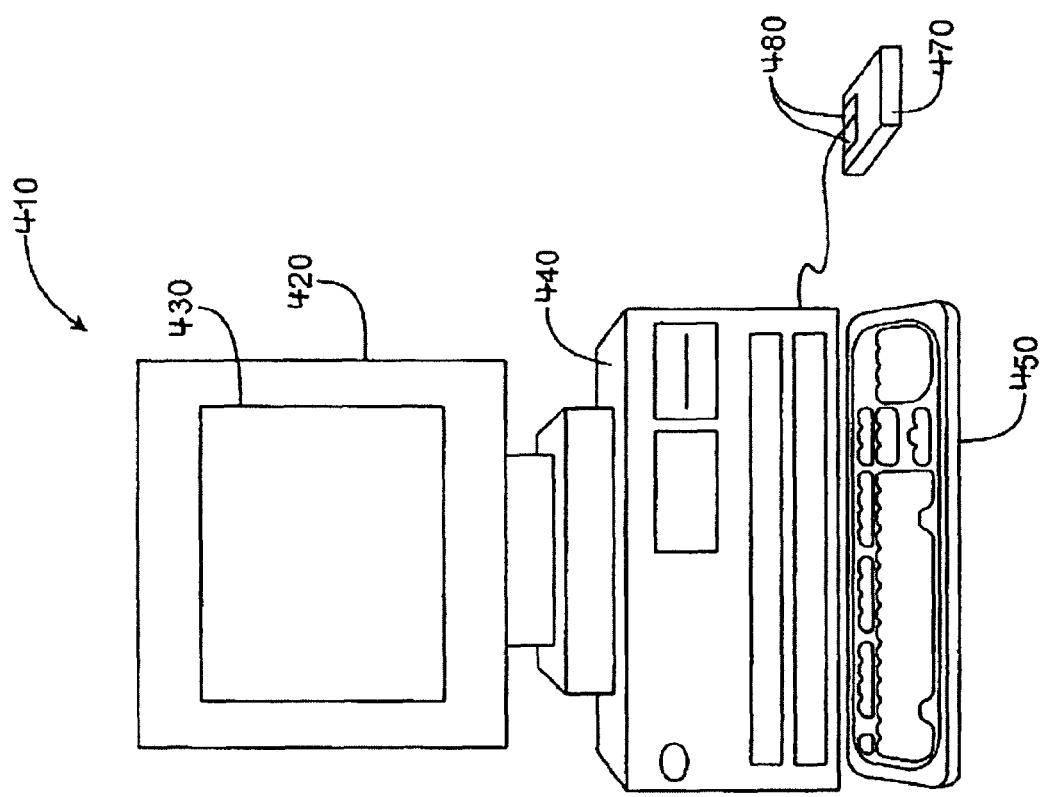
FIG. 4 is a schematic illustration of a computer system for in accordance with the teachings of the present invention.

As described above, one aspect of methods and systems in accordance with embodiments of the present invention, is the use of a single portal for providing access to healthcare information for multiple entities. In certain embodiments, this portal includes a website hosted by a server device configured to be in electronic communication with a computer network, for example the world wide web. FIG. 4 shows a simplified schematic diagram of an embodiment of a computer system for use in hosting such a healthcare information website portal. Alternatively or additionally, FIG. 4, and FIG. 4A may show parts of a client computer that is used by the patient to access the website.

A computer system 410 of FIG. 4 includes a monitor or display device 420, a display screen 430, a cabinet 440, a keyboard 450, and a mouse 470. The mouse 470 and the keyboard 450 are representative "user input devices." The mouse 470 includes buttons 480 for selection of buttons on a graphical user interface device. Other examples of user input devices are a touch screen, light pen, track ball, data glove, microphone, and so forth. FIG. 4 is representative of but one type of system for embodying the present invention. It will be readily apparent to one of ordinary skill in the art that many system types and configurations are suitable for use in conjunction with the present invention. In one embodiment, the computer system 410 includes an Intel class based computer, running a Windows® based operating system by Microsoft Corporation. However, the system is easily adapted to other operating systems and architectures by those of ordinary skill in the art without departing from the scope of the present invention.

As noted, the mouse 470 can have one or more buttons such as the buttons 480. The cabinet 440 houses familiar computer components such as disk drives, a processor, storage device, etc. Storage devices include, but are not limited to, disk drives, magnetic tape, solid state memory, bubble memory, etc. The cabinet 440 can include additional hardware such as input/output (I/O) interface cards for connecting the computer system 410 to external devices external storage, other computers or additional peripherals, further described below.

Figure 4A:
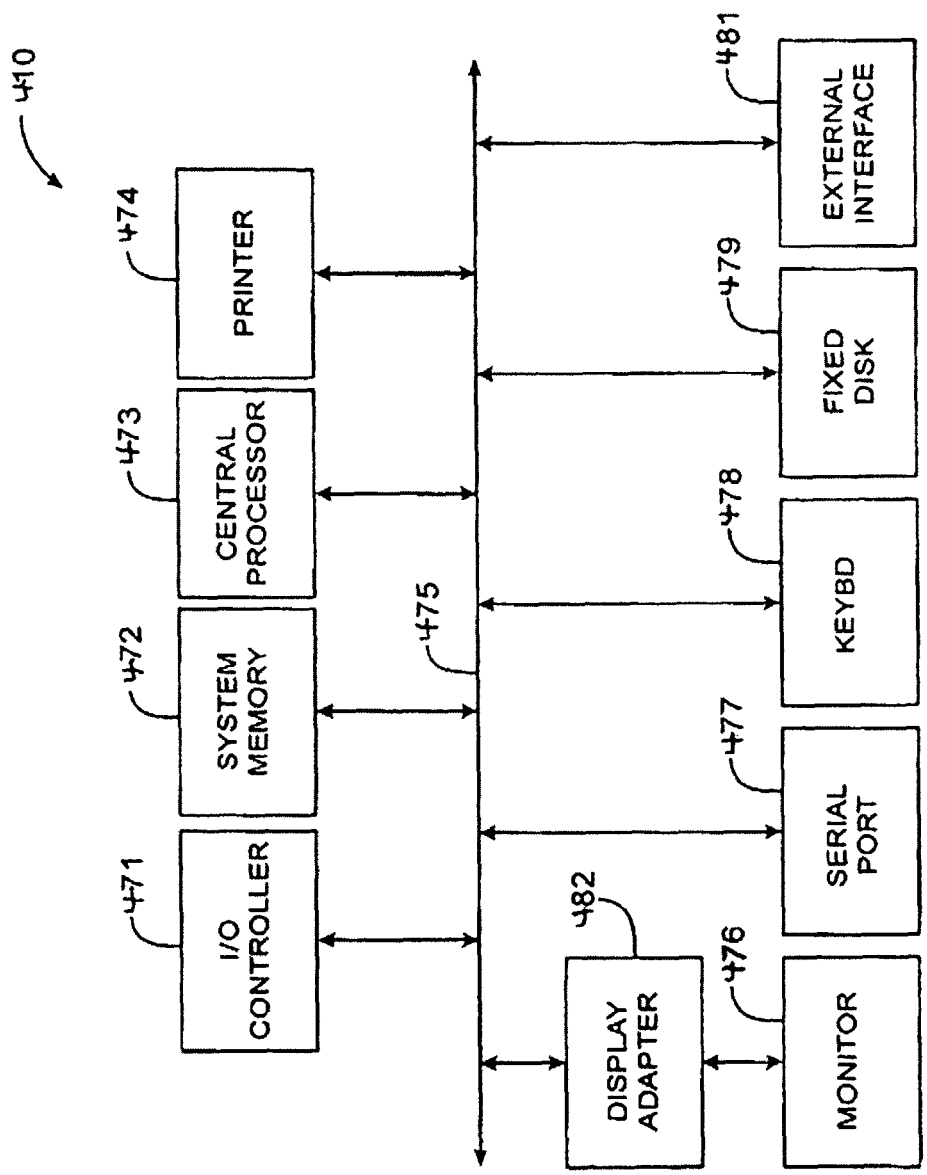
FIG. 4A is an illustration of basic subsystems the computer system of FIG. 4.

FIG. 4A is an illustration of basic subsystems in the computer system 410 of FIG. 4. This diagram is merely an illustration and should not limit the scope of the claims herein. One of ordinary skill in the art will recognize other variations, modifications, and alternatives. In certain embodiments, the subsystems are interconnected via a system bus 475. Additional subsystems such as a printer 474, a keyboard 478, a fixed disk 479, a monitor or display device 476, which is coupled to a display adapter 482, and others are shown. Peripherals and input/output (I/O) devices, which couple to I/O controller 471, can be connected to the computer system 410 by any number of means known in the art, such as a serial port 477. For example, the serial port 477 can be used to connect the computer system to an external interface device 48 (for example a modem), which in turn connects to a wide area network such as the Internet. The interconnection via the system bus 475 allows central processor 473 to communicate with each subsystem and to control the execution of instructions from system memory 472 or the fixed disk 479, as well as the exchange of information between subsystems. Other arrangements of subsystems and interconnections are readily achievable by those of ordinary skill in the art. System memory, and the fixed disk are examples of tangible media for storage of computer programs, other types of tangible media include floppy disks, removable hard disks, optical storage media such as CD-ROMS and bar codes, and semiconductor memories such as flash memory, read-only-memories (ROM), and battery backed memory.

Embodiments in accordance with the present invention offer a number of potential benefits over conventional systems for processing healthcare information. One advantage is the allowance for real-time access to the healthcare information. For the healthcare provider, this means that important information such as patient eligibility, the value of claims adjudicated by the healthcare insure, and medical records of the patient are readily accessible. For the healthcare insurance carrier, the availability of administered treatment and result information can lead to increased accuracy and fewer mistakes. Also, in embodiments of the invention, a patient may choose the privacy level associated with his or her medical information and can control access to that information by various providers.

Utilization of methods and embodiments in accordance with the present invention can also lead to greater efficiency in payments. Such payments executed with greater efficiency include Payer-to-Provider claims payments/accelerated payments, and Consumer-to-Provider co-payments and deductibles.

Utilization of methods and embodiments in accordance with the present invention can also lead to improved risk management. For example, the single portal provided for accessing healthcare information helps insure the accuracy and reliability of that information. Another source of improved risk management is the benefit of utilizing security and fraud controls associated with an payment processing network such as VisaNet™.

Utilization of methods and embodiments in accordance with the present invention can also function to improve the quality of the healthcare received. For example, the function of the healthcare portal to provide basic health information (portal), provider ratings, supplemental information, concierge services, and healthcare financial advice can allow for the maximum efficient utilization of the healthcare dollar, and ensure access to quality healthcare services.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

Incorporated by reference herein for all purposes are the following U.S. Nonprovisional patent application Ser. No. 10/418,989, filed Apr. 18, 2003 and entitled "SYSTEM AND METHOD FOR PAYMENT OF MEDICAL CLAIMS"; Ser. No. 11/231,026, filed Sep. 20, 2005 and entitled "METHOD FOR ENCODING MESSAGES BETWEEN TWO DEVICES FOR TRANSMISSION OVER STANDARD ONLINE PAYMENT NETWORKS"; Ser. No. 11/230,761, filed Sep. 20, 2005 and entitled "AUTO SUBSTANTIATION FOR OVER-THE-COUNTER TRANSACTIONS"; and Ser. No. 11/230,743, filed Sep. 20, 2005 and entitled "METHOD AND SYSTEM FOR DETERMINING HEALTHCARE ELIGIBILITY".

Other details of embodiments of the invention can be found in the following U.S. provisional patent applications, each of which are incorporated herein by reference in their entirety for all purposes: 60/641,483, filed on Jan. 4, 2005; 60/641,597, filed on Jan. 4, 2005; 60/641,464 filed on Jan. 4, 2005; 60/834,584, filed on Jul. 31, 2006; and 60/812,266, filed on Jun. 8, 2006.

One or more features from any embodiment may be combined with one or more features of any other embodiment without departing from the scope of the invention.

A recitation of "a", "an" or "the" is intended to mean "one or more" unless specifically indicated to the contrary.

All patents, patent applications, publications, and descriptions mentioned above are herein incorporated by reference in their entirety for all purposes and none is admitted to be prior art.

What is claimed is:

1. A method comprising:
    receiving a medical service eligibility inquiry message from a first healthcare provider via a payment processing network,
        the medical service eligibility inquiry message indicating a medical record information access request
        the payment processing network being configured to communicate, and process transactions using financial transaction credit card account originated communication message protocols having a financial interchange specification;
    retrieving a privacy level associated with a patient's medical record from a patient terminal, wherein the privacy level is designated to a first healthcare provider by a patient via a user interface of a host site, and the user interface of the host site is presented to the patient via the patient terminal;
    granting, by a host computer, the first healthcare provider access to the patient's medical record stored at a server and accessible through the user interface of the host site, based on the received privacy level, wherein the first healthcare provider has a different level of access to the patient's medical record than a second healthcare provider;
    obtaining the medical record information access request related to the first healthcare provider from the received medical service eligibility inquiry message, wherein the medical service eligibility inquiry message is sent upon triggering a portable consumer device at a financial payment acceptance terminal at the first healthcare provider who has access to the patient's medical record, the medical service eligibility inquiry message is sent through the payment processing network via an acquirer,
    wherein the payment processing network processes transactions between and amongst networks, wherein the acquirer is a financial institution with an account associated with the first healthcare provider;
    determining that the privacy level designated to the first healthcare provider grants the first healthcare provider access to the requested medical record information; and
    sending, according to the privacy level, the requested medical record information from the patient's medical record and co-payment information, to the first healthcare provider, in response to the medical record information access request from the received medical service eligibility inquiry message,
    wherein the requested medical record information and the co-payment information are transmitted through the payment processing network,
    wherein the medical information includes at least one of a medical condition, a medication history, a current medication, a treatment, a referral, a follow-up, or a medication.

2. The method of claim 1 wherein the payment processing system is specifically adapted to process medical and medical payment information.

3. The method of claim 1 wherein the privacy level allows the first healthcare provider to access patient eligibility information, patient co-payment information, patient deductible information, and patient balance owed post-adjudication,
    but not to access patient medical information such as medical treatments unrelated to an area of practice of the first healthcare provider, or the patient medical information not pertinent to a specific procedure performed or to be performed by the first healthcare provider.

4. The method of claim 1 wherein the patient's medical record is accessible on the host site to a healthcare insurance carrier.

5. The method of claim 4 further comprising setting a second privacy level governing access of the healthcare insurance carrier to the patient's medical record.

6. The method of claim 1 further comprising uploading the medical information to the host site through the payment processing network.

7. The method of claim 1 wherein the medical information is received in response to a healthcare claim message, communicated over the payment processing network from the first healthcare provider.

8. The method of claim 7 wherein the medical service eligibility inquiry message complies with HIPAA 270 and the healthcare claim message complies with HIPAA 837.

9. The method of claim 1, wherein the triggering occurs prior to treatment.

10. The method of claim 1, further comprising:
    after the patient receives a treatment, receiving feedback from the patient that relates to the treatment provided by the healthcare provider;
    incorporating, by the host computer, the feedback into a rating associated with the first healthcare provider; and
    providing the rating associated with the first healthcare provider to another patient.

11. The method of claim 10, wherein the rating associated with the first healthcare provider is communicated to the another patient through a hotline.

12. An apparatus comprising:
    a host computer including a processor in electronic communication with a computer readable storage medium, the computer readable medium having code stored thereon to direct the processor to:

receive a medical service eligibility inquiry message from a first healthcare provider via a payment processing network, the medical service eligibility inquiry message indicating a medical record information access request the payment processing network being configured to communicate, and process transactions using financial transaction credit card account originated communication message protocols having a financial interchange specification:

retrieve a privacy level associated with a patient's medical record via a host site, wherein the privacy level is designated to a first healthcare provider by a patient via a user interface of the host site, and the user interface of the host site is presented to the patient via a patient terminal, and wherein the privacy level provides the first healthcare provider with the ability to access the patient's medical record that is different from a second healthcare provider, grant the first healthcare provider access to the patient's medical record stored at a server and accessible through the host site, based on the received privacy level, obtain the medical record information access request related to the first healthcare provider from the received medical service eligibility inquiry message, wherein the medical record information access eligibility inquiry message is sent upon triggering a portable consumer device at a financial payment acceptance terminal at the first healthcare provider who has access to the patient's medical record, determine that the privacy level designated to the first healthcare provider grants the first healthcare provider access to the requested medical record information, and send information pertaining to the patient's medical record to the first healthcare provider who has access to the patient's medical record through the payment processing network, in response to the medical record information access request from the medical service eligibility inquiry message sent via an acquirer through the payment processing network, wherein the acquirer is a financial institution with an account associated with the first healthcare provider, wherein the triggering of the portable consumer device to the first healthcare provider causes the medical service eligibility inquiry message to be sent, wherein the information includes at least one of a medical condition, a medication history, a current medication, a treatment, a referral, a follow-up, or a medication.

13. The apparatus of claim 12 wherein the host site may be accessed by the first provider from the world wide web.

14. The apparatus of claim 12 wherein one privacy level allows the first provider to access certain medical records of the patient, but not to access other medical records designated as confidential by the patient.

15. The apparatus of claim 12 wherein the computer readable storage medium further comprises code allowing the first healthcare provider to update the patient's medical record.

16. The apparatus of claim 12 wherein the computer readable storage medium further comprises code allowing the first healthcare provider to upload medical information to the patient's medical record.

17. The apparatus of claim 12 wherein the computer readable storage medium further comprises code allowing the host computer to be accessed based upon the portable consumer device authenticated to the patient.

18. The apparatus of claim 17 wherein the payment processing network is specifically adapted to process debit and credit card transactions.

19. A non-transitory computer readable medium storing computer-executable instructions executable by a processor to:

receive a medical service eligibility inquiry message from a first healthcare provider via a payment processing network, the medical service eligibility inquiry message indicating a medical record information access request the payment processing network being configured to communicate, and process transactions using financial transaction credit card account originated communication message protocols having a financial interchange specification;

retrieve a privacy level associated with a patient's medical record via a host site, wherein the privacy level is designated to a first healthcare provider by a patient via a user interface of the host site, and the user interface of the host site is presented to the patient via a patient terminal, and wherein the privacy level provides the first healthcare provider with the ability to access the patient's medical record that is different from a second healthcare provider with access to the medical record;

grant the first healthcare provider access to the patient's medical record stored at a server and accessible through the host site, based on the received privacy level;

determine a medical record information access request related to the first healthcare provider from the received medical service eligibility inquiry message, wherein the medical record information access eligibility inquiry message is sent upon triggering a portable consumer device at a financial payment acceptance terminal at the first healthcare provider who has access to the patient's medical record;

determine that the privacy level designated to the first healthcare provider grants the first healthcare provider access to the requested medical record information; and send information pertaining to the patient's medical record to the first healthcare provider who has access to the patient's medical record through the payment processing network, in response to the medical record information access request from the medical service eligibility inquiry message sent via an acquirer through the payment processing network, wherein the acquirer is a financial institution with an account associated with the first healthcare provider, wherein the triggering of the portable consumer device to the first healthcare provider causes the medical service eligibility inquiry message to be sent, wherein the information includes at least one of a medical condition, a medication history, a current medication, a treatment, a referral, a follow-up, or a medication.

20. The computer readable storage medium of claim 19 further comprising code allowing the first healthcare provider to update the patient's medical record.

21. The computer readable storage medium of claim 19 further comprises code allowing the first healthcare provider to upload medical information to the patient's medical record.

22. The computer readable storage medium of claim 19 further comprising code allowing the host computer to be accessed based upon the portable consumer device authenticated to the patient.

23. A method for management of healthcare information, the method comprising the steps of:
  receiving a medical service eligibility inquiry message from a first healthcare provider via a payment processing network,
    the medical service eligibility inquiry message indicating a medical record information access request
    the payment processing network being configured to communicate, and process transactions using financial transaction credit card account originated communication message protocols having a financial interchange specification;
  retrieving a plurality of access authorization levels based on a type of healthcare information needed for a patient by a healthcare provider,
    wherein the plurality of access authorization levels are specified by a patient via a user interface of a host site and include a first access authorization level and a second access authorization level,
    wherein the first access authorization level and the second access authorization level are associated with different healthcare providers and grant different levels of access to the patient's medical record;
    wherein the medical record information access eligibility inquiry message is sent upon triggering a portable device at a financial payment acceptance terminal at the healthcare provider who has access to the patient's medical record,
    wherein the patient provides the healthcare provider with access to the healthcare information using the portable device and wherein the level of access is based on the first access authorization level, and
    wherein the healthcare information is stored at a server and accessible through the host site and includes medical information and co-payment information, wherein the medical information includes at least one of: a medical condition, a medication history, a current medication, a treatment, a referral, a follow-up, or a medication;
  obtaining the medical record information access request related to the healthcare provider from the received medical service eligibility inquiry message;
  determining that the privacy level designated to the healthcare provider grants the healthcare provider access to the requested medical record information;
  sending, by the payment processing network, the healthcare information to the healthcare provider after receiving the medical service eligibility inquiry message including the medical record information access request received from an acquirer that is a financial institution with an account associated with the healthcare provider; and
  transacting, by the payment processing network, a payment to the healthcare provider for a service rendered to the patient using the portable device.

24. The method of claim 23, wherein the eligibility inquiry message is routed from a third party interface.

25. An electronic medical record retrieval processor-implemented method, comprising:
  obtaining, via a payment processing network being configured to communicate, and process transactions using financial transaction credit card account originated communication message protocols having a financial interchange specification, a medical service eligibility inquiry message from a first healthcare provider,
    the medical service eligibility inquiry message being generated upon an instantiation of a consumer payment device at a financial payment acceptance terminal located at the first healthcare provider,
    the medical service eligibility inquiry message indicating a medical record information access request;
  obtaining patient identifying information from the medical service eligibility inquiry message;
  retrieving medical record privacy settings associated with a patient's medical record,
    the medical record privacy settings including a first privacy level designated to the first healthcare provider and a second privacy level designated to a second healthcare provider,
    the medical record privacy settings being provided by a patient via a user interface of a host site, and the user interface of the host site is presented to the patient via a patient terminal;
  determining the first privacy level grants the first healthcare provider access to the patient's medical record stored at a server and accessible through the user interface of the host site,
    wherein the second privacy level indicates access restriction for the second healthcare provider to access the patient's medical record;
  sending, the requested medical record information from the patient's medical record and co-payment information, to the first healthcare provider, in response to the medical record information access request from the received medical service eligibility inquiry message,
    wherein the requested medical record information and the co-payment information are transmitted through the payment processing network,
    wherein the medical information includes at least one of a medical condition, a medication history, a current medication, a treatment, a referral, a follow-up, or a medication.

* * * * *